United States Patent
Hallinan et al.

(10) Patent No.: US 9,822,054 B2
(45) Date of Patent: Nov. 21, 2017

(54) USE OF A RUTHENIUM PROMOTER IN A PHOSPHINE OXIDE CARBONYLATION PROCESS

(71) Applicant: LyondellBasell Acetyls, LLC, Houston, TX (US)

(72) Inventors: Noel C. Hallinan, Loveland, OH (US); David L. Ramage, Friendswood, TX (US); Daniel F. White, Houston, TX (US)

(73) Assignee: LyondellBasell Acetyis, LLC, Houston, TX (US)

( * ) Notice: Subject to any disclaimer, the term of this patent is extended or adjusted under 35 U.S.C. 154(b) by 40 days.

(21) Appl. No.: 14/997,654

(22) Filed: Jan. 18, 2016

(65) Prior Publication Data

US 2016/0207863 A1    Jul. 21, 2016

Related U.S. Application Data

(60) Provisional application No. 62/105,572, filed on Jan. 20, 2015.

(51) Int. Cl.
   *C07C 51/12*    (2006.01)
(52) U.S. Cl.
   CPC .................................. *C07C 51/12* (2013.01)

(58) Field of Classification Search
   None
   See application file for complete search history.

(56) References Cited

U.S. PATENT DOCUMENTS

| | | |
|---|---|---|
| 6,031,129 A | 2/2000 | Hinnenkamp et al. |
| 6,573,403 B1 | 6/2003 | Joensen |
| 7,053,241 B1 | 5/2006 | Torrence |
| 2006/0173212 A1 | 8/2006 | Gaemers et al. |

FOREIGN PATENT DOCUMENTS

EP    0072055 A1    2/1983

OTHER PUBLICATIONS

International Search Report and Written Opinion dated Mar. 11, 2016 for PCT/US2016/013790.

*Primary Examiner* — Sudhakar Katakam
*Assistant Examiner* — Ana Z Muresan

(57) ABSTRACT

The present technology relates to a rhodium catalyzed carbonylation process of alcohols, ethers, and esters in the presence of phosphine oxide and ruthenium additives to produce carboxylic acids. In some embodiments, the technology provides for an improved method of preparing acetic acid from methyl acetate or methanol using a rhodium catalyst with a phosphine oxide and a ruthenium additive.

18 Claims, No Drawings

USE OF A RUTHENIUM PROMOTER IN A PHOSPHINE OXIDE CARBONYLATION PROCESS

CROSS-REFERENCE TO RELATED APPLICATIONS

This application claims benefit of priority to U.S. Provisional Application No. 62/105,572 filed on Jan. 20, 2015, which is incorporated herein by reference in its entirety.

BACKGROUND OF THE INVENTION

I. Field of the Invention

The present disclosure relates to the field of chemistry. In some aspects, the present disclosure relates to carbonylation reactions and methods of producing carboxylic acids.

II. Description of Related Art

Rhodium catalyzed carbonylation is a widely used process to produce carboxylic acids such as acetic acid. In particular, this process is used commercially to produce glacial acetic acid. Quantum Chemical Company described the use of pentavalent complexes such as tri-substituted phosphine oxides to improve the conversion rate of methyl acetate to acetic acid without the need to introduce high concentrations of water.

The activity of a rhodium carbonylation catalyst is reduced over time as the catalyst tends to precipitate under the carbonylation conditions and leads to decreased activity over time. Addition of ruthenium to the catalytic mixture has been shown to stabilize the rhodium catalyst and increase the carbonylation rate when using a rhodium catalyst. This increased rate has been shown under both high water and low water carbonylation conditions. The incorporation of triphenylphosphine oxide into the carbonylation process has been shown to lead to improved catalytic carbonylation system. Thus, a catalytic system which has an improved conversion rate while stabilizing the rhodium carbonylation catalyst so that it has an increased catalytic lifetime is commercially desirable.

SUMMARY OF THE INVENTION

In one aspect, the present disclosure provides for a method for producing carboxylic acids. In some embodiments, the method comprises reacting:
  (A) a starting material selected from methanol, dimethyl ether, or methyl acetate;
  (B) carbon monoxide (CO); and
  (C) a rhodium compound;
in a reaction mixture in the presence of a ruthenium compound, a first iodide source, and a phosphine oxide$_{(C \leq 24)}$ under conditions sufficient to cause carbonylation to produce a reaction product comprising acetic acid. In some embodiments, the rhodium compound is rhodium(II) acetate, rhodium(III) acetate, $Rh_2(CO)_4I_2$, $Rh_2(CO)_4Br_2$, $Rh_2(CO)_4Cl_2$, or $[H][Rh(CO)_2I_2]$. In some embodiments, the ruthenium compound is ruthenium acetate or ruthenium iodide. In some embodiments, the phosphine oxide$_{(C \leq 24)}$ is triphenylphosphine oxide. In some embodiments, the method comprises maintaining greater than 10 equivalents of the phosphine oxide$_{(C \leq 24)}$ relative to the rhodium complex in the reaction mixture. In some embodiments, the method comprises maintaining greater than 50 equivalents of the phosphine oxide$_{(C \leq 24)}$ relative to the rhodium complex in the reaction mixture. In some embodiments, the methyl acetate is maintained at a concentration from about 0.1 M to about 5 M. In some embodiments, the first iodide source is hydroiodic acid. In some embodiments, the method comprises maintaining the first iodide source at a concentration from about 0.05 M to about 2.0 M. In some embodiments, the method further comprises adding a second iodide source. In some embodiments, the second iodide source is methyl iodide. In some embodiments, the method comprises maintaining the second iodide source at a concentration from about 0.05 M to about 3 M. In some embodiments, the method further comprises adding water to the reaction. In some embodiments, the water is maintained at a concentration less than 7.5 M. In some embodiments, the method comprises heating the reaction to a temperature from about 50° C. to about 300° C. In some embodiments, the method comprises running the reaction at a pressure from about 200 psi to about 600 psi. In some embodiments, the method further comprises adding hydrogen gas to the reaction.

In another aspect, the present disclosure provides for a method comprising:
  (A) admixing a starting material selected from an alcohol$_{(C \leq 12)}$, an ester$_{(C \leq 15)}$, or an ether$_{(C \leq 24)}$ with a rhodium compound, a ruthenium compound, an iodide source, and a phosphine oxide$_{(C \leq 24)}$ to form a first reaction mixture;
  (B) pressurizing the first reaction mixture with carbon monoxide to form a second reaction mixture; and
  (C) reacting the starting material with the rhodium compound and the carbon monoxide in the presence of the ruthenium compound, the iodide source, and the phosphine oxide$_{(C \leq 24)}$ under conditions sufficient to cause carbonylation to produce a reaction product comprising a carboxylic acid$_{(C2-13)}$.

In some embodiments, the carboxylic acid$_{(C2-13)}$ is acetic acid. In some embodiments, the ester$_{(C \leq 15)}$ is methyl acetate. In some embodiments, the ether$_{(C \leq 24)}$ is dimethyl ether. In some embodiments, the alcohol$_{(C \leq 12)}$ is methanol.

In still another aspect, the present disclosure provides for a method comprising:
  (A) adding an rhodium compound, a ruthenium compound, an iodide source, a phosphine oxide$_{(C \leq 24)}$, and a starting material selected from an alcohol$_{(C \leq 12)}$, an ester$_{(C \leq 15)}$, or an ether$_{(C \leq 24)}$ to a reactor to form a first reaction mixture;
  (B) pressurizing the reactor with carbon monoxide to produce a second reaction mixture; and
  (C) contacting the starting material selected from an alcohol$_{(C \leq 12)}$, an ester$_{(C \leq 15)}$, or an ether$_{(C \leq 24)}$ with the rhodium compound and the carbon monoxide in the presence of the ruthenium compound, the iodide source, and the phosphine oxide$_{(C \leq 24)}$ in the reactor under conditions sufficient to cause carbonylation to produce a reaction product comprising a carboxylic acid$_{(C2-13)}$.

In some embodiments, the carboxylic acid$_{(C2-13)}$ is acetic acid. In some embodiments, the ester$_{(C \leq 15)}$ is methyl acetate. In some embodiments, the ether$_{(C \leq 24)}$ is dimethyl ether. In some embodiments, the alcohol$_{(C \leq 12)}$ is methanol.

While multiple embodiments are disclosed, still other embodiments will become apparent to those skilled in the art from the following detailed description. As will be apparent, certain embodiments, as disclosed herein, are capable of modifications in various aspects, all without departing from the spirit and scope of the claims as presented herein. Accordingly, the drawings and detailed description are to be regarded as illustrative in nature and not restrictive.

DETAILED DESCRIPTION OF THE INVENTION

In some aspects, the present disclosure provides for a method of producing a carboxylic acid comprising the carbonylation of an alcohol or ester in the presence of a rhodium catalyst with a phosphine oxide and ruthenium promoter. In some embodiments, the use of a phosphine oxide with a ruthenium promoter increases the catalyst lifespan while increasing the catalyst activity. In some embodiments, the use of both additives in the carbonylation process leads to an increased rate of carboxylic acid production, an increased yield of carboxylic acid, and/or a decreased production of by-products such as long chain carboxylic acids.

I. Carbonylation Methods

In some aspects, the present disclosure provides for a method of carbonylation of an alcohol or an ester with a rhodium catalyst and a ruthenium promoter and a phosphine oxide to produce a carboxylic acid. In some embodiments, the process is a method of producing acetic acid comprising the carbonylation of methyl acetate or methanol. In some embodiments, the method comprises using methyl acetate as the starting material. In other embodiments, the method comprises using methanol as the starting material. In other embodiments, the method comprises using dimethyl ether.

In another aspect, the present disclosure provides for a carbonylation process which uses a transition metal catalyst. In some embodiments, the transition metal catalyst is a rhodium catalyst. It is contemplated that any known rhodium carbonylation catalyst may be used in the carbonylation process described herein. In some aspects, the rhodium catalyst comprises a rhodium source selected from rhodium metal, rhodium halides, rhodium oxide, rhodium acetate, organorhodium compounds, coordination compounds of rhodium or similar compounds. Additionally, mixtures of different rhodium sources may be used. Non-limiting examples of rhodium sources which can be used in the carbonylation process of the present disclosure include $RhCl_3$, $RhBr_3$, $RhI_3$, $RhCl_3.3H_2O$, $RhBr_3.3H_2O$, $RhI_3.3H_2O$, $Rh_2(CO)_4Cl_2$, $Rh_2(CO)_4Br_2$, $Rh_2(CO)_4I_2$, $Rh_2(CO)_8$, $Rh(CH_3CO_2)_2$, $Rh(CH_3CO_2)_3$, $Rh[(C_6H_5)_3P]_2(CO)I$, $Rh[(C_6H_5)_3P]_2(CO)Cl$, elemental Rh, $Rh(NO_3)_3$, $Rh(SnCl_3)$ $[(C_6H_5)P]_2$, $RhCl(CO)[(C_6H_5)As]_2$, $RhI(CO)[(C_6H_5)Sb]_2$, $Rh[(C_6H_5)_3P]_2(CO)Br$, $Rh[(n-C_4H_9)_3P]_2(CO)Br$, $Rh[(n-C_4H_9)_3P]_2(CO)I$, $RhBr[(C_6H_5)_3P]_3$, $RhI[(C_6H_5)_3P]_3$, $RhCl[(C_6H_5)_3P]_3$, $RhCl[(C_6H_5)_3P]_3H_2$, $[(C_6H_5)_3P]_3Rh(CO)H$, $Rh_2O_3$, $[Rh(C_3H_4)_2Cl]_2$, $K_4Rh_2Cl_2(SnCl_2)_4$, $K_4Rh_2Br_2(SnBr_2)_4$, $[H][Rh(CO)_2I_2]$, $K_4Rh_2I_2(SnI_2)_4$ or is a complex of the formula $[Rh(CO)_2X_2][Y]$, wherein X is a halide and Y is a proton, hydrogen, an alkali metal cation, or a quaternary compound of nitrogen, phosphorus, or arsenic, or is a similar rhodium complex. In some embodiments, the rhodium source is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ or $[H][Rh(CO)_2I_2]$. In some embodiments, the rhodium source is $Rh(CH_3CO_2)_2$, $Rh(CH_3CO_2)_3$ or $[H][Rh(CO)_2I_2]$.

The rhodium compound or complex of the present disclosure may be used in a concentration sufficient to achieve a reasonable amount of carbonylation or an effective rate of carbonylation. Without being bound by theory, excess amounts of the rhodium catalyst can lead to undesired by-products. Thus, the optimization of the rhodium catalyst is one factor which can directly impact the rate, amount and yield of the desired carbonylation product. In a carbonylation process, the concentration of the rhodium catalyst that may be used is from 10 ppm to about 4000 ppm, based upon the total weight of the liquid reaction component. In some embodiments, the amount of catalyst is from about 200 ppm to about 1200 ppm. In some embodiments, the amount of catalyst is from about 400 ppm to about 1000 ppm. These concentrations can also be expressed using molarity. In some embodiments, the concentration is from about $1\times10^{-4}$ M to about $4\times10^{-2}$ M, based upon the total volume of the liquid reaction component. In some embodiments, the concentration is from about $2\times10^{-3}$ M to about $1.2\times10^{-2}$ M. In some embodiments, the concentration is from about $4\times10^{-3}$ M to about $1\times10^{-2}$ M. While these concentrations are sufficient to cause carbonylation to proceed, higher concentrations may be used so long as the higher concentrations do not produce an unsatisfactory level of by-products.

It is envisioned that in some aspects, the present disclosure relates to a carbonylation method that is conducted in the liquid phase. In other embodiments, the carbonylation method is conducted in the gas phase. In some embodiments, the carbonylation reaction contains one or more liquid components. In some embodiments, the liquid components are selected from acetic acid, methanol, water, methyl iodide or methyl acetate. In some embodiments, the liquid components include more than one of acetic acid, water, methyl iodide or methyl acetate. In some embodiments, the liquid components are added as a liquid but vaporize under the reaction conditions.

In some aspects, the carbonylation reaction comprises adding methyl acetate as a reaction component. In some embodiments, the amount of methyl acetate maintained in the liquid reaction component comprises from about 0.5 to about 10 wt. %, based upon the total weight of the liquid reaction component. In some embodiments, the methyl acetate weight percentage correlates to a molarity of the methyl acetate from about 0.07 M to about 1.4 M. In some embodiments, the amount of methyl acetate maintained in the liquid reaction component is from about 1 to about 8 wt. %, based upon the total weight of the of the liquid reaction component. In some embodiments, the methyl acetate can be charged into the reactor. In other embodiments, the methyl acetate is formed in situ. Additionally, in some embodiments, the amount of methyl acetate is maintained to achieve a desired ratio between methyl acetate and the rhodium catalyst. In some embodiments, the ratio of methyl acetate to the rhodium metal catalyst is from about 1000:1 to about 2:1. In some embodiments, the ratio of methyl acetate to rhodium metal catalyst is from about 700:1 to about 5:1. In some embodiments, the ratio of methyl acetate to rhodium metal catalyst is from about 275:1 to about 14:1.

In some aspects, the present disclosure comprises a liquid medium comprises an iodide source. In some embodiments, the iodide source is a methyl iodide or hydroiodic acid. In some embodiments, the iodide source is methyl iodide. In some embodiments, the methyl iodide is added directly to the reaction mixture. In other embodiments, the methyl iodide can be generated in situ from the reaction of hydroiodic acid with methanol. Without being bound by theory, it is believed that the methyl iodide disproportionates and adds to the rhodium catalyst as a methyl cation and an iodide anion to form the active catalyst complex. A variety of different concentrations of the iodide source may be used in the carbonylation reaction of the present disclosure. The optimization of the iodide source would be routine for a person of skill in the art. In some embodiments, the amount of methyl iodide maintained in the reaction comprises a concentration from about 0.6 to about 36 wt. %, based upon the total weight of the liquid reaction component. In some embodiments, the amount of methyl iodide is from about 3.6 to about 24 wt. %, based upon the total weight of the liquid reaction component. The amount of methyl iodide can also be determined as a molarity of the liquid reaction component. In some embodiments, the concentration of methyl iodide is from about 0.05 M to about 3.0 M. In some embodiments, the concentration of methyl iodide is from 0.3 M to about 2.0 M. In other embodiments of the present disclosure, hydroiodic acid is used as the iodide source. In some embodiments, the concentration of hydroiodic acid used in the carbonylation reaction is from about 0.6 to about 23 wt. %, based upon the total weight of the liquid reaction component. In some embodiments, the concentration of hydroiodic acid is from about 2.3 to about 11.6 wt. %, based upon the total weight of the liquid reaction component. As with the concentration of methyl iodide, the concentration of hydroiodic acid can also be measured as the molarity of the liquid reaction component. In some embodiments, the concentration of hydroiodic acid is from about 0.05 M to about 2.0 M. In some embodiments, the concentration of hydroiodic acid is from about 0.2 M to about 1.0 M.

In some aspects, the carbonylation reaction further comprises adding a carboxylic acid to the liquid reaction component. In some embodiments, the carboxylic acid is acetic acid. In some embodiments, the concentration of acetic acid maintained in the liquid reaction component is from 20 to about 80 wt. % or, when measured in molarity, from about 3.0 M to about 12.0 M. In some embodiments, the amount of acetic acid is from about 35 to about 65 wt. % or, when measured in molarity, is from about 5 M to about 10 M. In some embodiments, the balance of the liquid reaction component is acetic acid.

In some aspects, the carbonylation reaction further comprises adding a second metal compound to the reaction mixture. In other embodiments, the carbonylation reaction further comprises adding one or more compound or complex of a metal selected from ruthenium, rhenium, osmium, cadmium, zinc, mercury, gallium, indium or tungsten. In some embodiments, the metal is ruthenium, osmium or rhenium. In some embodiments, the metal is ruthenium. In some embodiments, any soluble or heterogeneous source of ruthenium can be added to the reaction mixture to enhance the yield and production of the carbonylation process. Some non-limiting examples of ruthenium compounds or complexes that can be used in a carbonylation reaction of the present disclosure include ruthenium halides, ruthenium carbonyl, ruthenium oxides, ruthenium carboxylates, ruthenium nitrates, ammonium salts of ruthenium, ruthenium carbonyl complexes, organoruthenium complexes such as tetrachlorobis(benzene)diruthenium(II), dichloro(cycloocta-1,5-diene) ruthenium(II) polymer, or tetrachlorobis(4-cumene)diruthenium(II) or mixed ruthenium halocarbonyls compounds such as dichlorotricarbonylruthenium(III) dimer or dibromotricarbonyl-ruthenium(II) dimer. Other examples of potential ruthenium compounds or complexes are described in U.S. Pat. No. 7,053,241. In some embodiments, the ruthenium compound or complex is ruthenium acetate or ruthenium iodide. In some embodiments, the ruthenium compound or complex is ruthenium acetate. In some embodiments, the concentration of the second metal maintained in the liquid reaction component is maintained relative to the carbonylation catalyst. In some embodiments, the amount of the second metal relative to the carbonylation catalyst is from about 0.1:1 to about 20:1. In some embodiments, the amount is from about 0.5:1 to 10:1. In some embodiments, the amount is from about 2:1 to about 10:1. In some embodiments, the second metal is added to the reaction medium up to the limit of solubility of the second metal in the reaction mixture. In some embodiments, the concentration of the second metal is less than about 8000 ppm. In some embodiments, the concentration of the second metal is from about 400 ppm to about 7000 ppm.

In some aspects, the amount of water added to the carbonylation reaction can be used to control the rate of the reaction along with other reaction components. In some embodiments, the water is added deliberately to the reaction mixture. In other embodiments, the water is a contaminant from the addition of other components. In some embodiments, the carbonylation reaction comprises reacting the carbon monoxide and the alcohol or reactive component with water at a low water concentration. Without being bound by theory, the addition of water promotes the final conversion of the carbonylated compound into the appropriate carboxylic acid. In some embodiments, the low water concentration is less than about 20 wt. % or 12.5 M. In some embodiments, the low water concentration is less than about 14 wt. % or 8.75 M. In some embodiments, the low water concentration is less than about 4 wt. % or 2.5 M. In some embodiments, low water concentration comprises maintaining water in the reactor from about 0.1 wt. % or 62.5 mM to about 10 wt. % or 11.25 M. In some embodiments, the low water concentration is from about 0.2 wt. % or 125 mM to about 5 wt. % or 3.125 M. In some embodiments, the low water concentration is from about 0.5 wt. % or 312.5 mM to about 2.5 wt. % or 1.5625 M. In some embodiments, the low water concentration is from about 1.5 wt. % or 937.5 mM to about 2.5 wt. % or 1.5625 M. In other embodiments, the reaction has a high water concentration. In some embodiments, the high water concentration is greater than about 4 wt. % or 2.5 M. In some embodiments, the high water concentration is greater than about 14 wt. % or 8.75 M. In general, the carbonylation method when the carbonylation method comprises an iodide salt then the amount of water used is less than 10 wt. % or 6.25 M. In some embodiments, additional water is formed in situ during the reaction process. The amount of water can, in some embodiments, be measured relative to the amount of catalyst used in the reaction. In some embodiments, the ratio of water to catalyst is from about 200:1 to about 4000:1. In some embodiments, the ratio is from about 270:1 to about 1750:1.

In some aspects, the present disclosure includes a carbonylation process which further comprises the addition of one or more gaseous compounds to the reaction mixture. In one embodiment, hydrogen gas is added to the reaction mixture. Without being bound by theory, the addition of hydrogen to the reaction mixture, such as a reaction mixture comprising a rhodium catalyst, is believed to decrease the selectivity of the carbonylation process to producing by-product aldehydes and alcohols. Furthermore, without being bound by theory, carbonylation reactions which comprise hydrogen also may exhibit increased catalytic efficacy. The amount of hydrogen gas depends on the catalyst and other reactive metal components employed as well as the desired products. In some embodiments, the ratio of hydrogen relative to the CO in the reaction mixture is from about 2:1 to about 1:8. In some embodiments, the ratio of hydrogen relative to the compound of CO is from about 1:1 to about 1:4. In some embodiments, the concentration of the hydrogen gas maintained in the reaction mixture is from about 0.1 mol % to about 5 mol % based upon the amount of CO added to the reactor. In some embodiments, the concentration of hydrogen is from about 0.5 mol % to about 3 mol %. In some embodiments, the hydrogen gas is added to the reactor as a separate stream from the other gaseous components. In other embodiments, the hydrogen gas is added as a mixture with CO. In some embodiments, hydrogen gas can be added to the reaction mixture as needed in order to maintain a consistent concentration of hydrogen gas in the reaction mixture. As CO is consumed in the reaction, in some embodiments, the molar ratio of hydrogen to CO can increase to a concentration from about 1000:1 to about 100:1. As the molar ratio of hydrogen to CO changes, in some embodiments, more CO is added to the reaction mixture to increase the molar ratio of hydrogen to CO.

In some aspects, the present disclosure provides for a carbonylation reaction which comprises adding CO to the reaction mixture. In some embodiments, the CO can be added as a gas. In other embodiments, the CO is generated in situ from the ligands of one or more of the metal catalysts. In some embodiments, CO is maintained at a pressure from about 10 psig (69 kPa) to about 800 psig (about 5,515 kPa). In some embodiments, CO is maintained at a pressure from about 50 psig (about 344 kPa) to about 500 psig (about 3,447 kPa). In some embodiments, CO is maintained at a pressure from about 100 psig (about 689 kPa) to about 300 psig (about 2,068 kPa). In some embodiments, the reaction comprises continuous addition of CO to the reaction mixture to maintain a constant molar ratio of CO as the CO is consumed in the reaction.

In some aspects, the present disclosure provides a carbonylation process which can be carried out using a wide variety of different reactor systems. In some embodiments, the carbonylation process is carried out in a batch mode reactor. In other embodiments, the carbonylation process is carried out in a continuous mode reactor. In other embodiments, the carbonylation process is carried out in a fixed bed or fluidization reactor.

The carbonylation method of the present disclosure is conducted under an increased pressure. In some embodiments, the reaction pressure is from about 200 psig (about 1,378 kPa) to about 1200 psig (about 8,274 kPa). In some embodiments, the reaction pressure is from about 300 psig (about 2,068 kPa) to about 600 psig (about 4,137 kPa). In some embodiments, the reaction pressure is about 400 psig (2,758 kPa). Additionally, the temperature of the carbonylation reaction is elevated above room temperature. In some embodiments, the temperature of the carbonylation reaction is greater than 100° C. In some embodiments, the temperature is from about 150° C. to about 225° C. In some embodiments, the temperature is from about 160° C. to about 220° C. In some embodiments, the temperature is from about 170° C. to about 200° C. In some embodiments, the temperature is about 175° C.

The method of the present disclosure includes the use of a phosphine oxide in production of a carboxylic acid in an amount relative to the rhodium catalyst. It is contemplated that any amount of phosphine oxide may be used in the reaction process. In some embodiments, the amount of phosphine oxide is greater than 50 equivalents per equivalent of rhodium catalyst. In some embodiments, the amount of phosphine oxide is greater than 100 equivalents per equivalent of rhodium catalyst. The amount of phosphine oxide used can also be described in terms of a concentration of the reaction mixture. In some embodiments, the amount of phosphine oxide used is from about 0.2 M to about 3.0 M. In some embodiments, the amount of phosphine oxide used is from about 0.4 M to about 1.4 M. In some embodiments, the concentration of the phosphine oxide is sufficient to achieve an improvement in some process metric such as increased rate, increased yield, or decreased production of one or more by-products. Without being bound by theory, the addition of phosphine oxide prevents the precipitation of the active rhodium catalyst and thus maintains the rate of the carbonylation reaction.

II. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

III. Definitions

When used in the context of a chemical group: "hydrogen" means —H; "hydroxy" means —OH; "carboxy" means —C(=O)OH (also written as —COOH or —CO$_2$H); "halo" means independently —F, —Cl, —Br or —I; and "amino" means —NH$_2$. When used in the context of a chemical group: "halide" means a halogen atom formulated as an anion bearing a single negative charge. When used in the context of a ligand, "carbonyl" means "CO".

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. It is noted that while the alkenediyl group is aliphatic, once connected at both ends, this group is not precluded from forming an aromatic structure. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro-group and no other atoms aside from carbon, hydrogen and fluorine are present.

Similar to the term "alkyl" defined above, other chemical groups are defined according to standard IUPAC nomenclature in combination with the general descriptions shown below. The term "alkenyl" refers to a monovalent unsaturated aliphatic group with a carbon atom as the point of attachment, a linear or branched acyclic structure, at least one nonaromatic carbon-carbon double bond, no carbon-carbon triple bonds, and no atoms other than carbon and hydrogen. The term "aryl" refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused.

As used herein, the term does not preclude the presence of one or more alkyl or aralkyl groups (carbon number limitation permitting) attached to the first aromatic ring or any additional aromatic ring present. The term "aralkyl" refers to the monovalent group -alkanediyl-aryl, in which the terms alkanediyl and aryl are each used in a manner consistent with the definitions herein and standard IUPAC nomenclature. The term "heteroaryl" refers to a monovalent aromatic group with an aromatic carbon atom or nitrogen atom as the point of attachment, said carbon atom or nitrogen atom forming part of one or more aromatic ring structures, wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. When any of these terms is used with the "substituted" modifier, one or more hydrogen atom(s) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The suffix "diyl" on a chemical group refers to the divalent group form of that chemical group.

The term "alkoxy," when used without the "substituted" modifier, refers to the group —OR, in which R is an alkyl, as that term is defined above. The terms "cycloalkoxy", "alkenyloxy", "aryloxy", "aralkoxy", and "heteroaryloxy", when used without the "substituted" modifier, refers to groups, defined as —OR, in which R is cycloalkyl, alkenyl, aryl, aralkyl, and heteroaryl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. The term "ester" corresponds to a group of the formula: RC(O)R', wherein R is an alkyl group and R' is an alkoxy group. The term "carboxylic acid" corresponds to a group of the formula: RC(O)OH, wherein R is an alkyl group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "phosphine oxide," when used without the "substituted" modifier, refers to a compound of the formula O=PR$_3$ or a diphosphine oxide as that term is defined below, wherein each R is independently hydrogen, alkyl, cycloalkyl, alkenyl, aryl, aralkyl, or heteroaryl as those terms are defined above. Non-limiting examples include OPMe$_3$ (trimethylphosphine oxide) and PPh$_3$O (triphenylphosphine oxide). The term "diphosphine oxide," when used without the "substituted" modifier, refers to a compound of the formula R$_2$—P(O)-L-P—R$_2$ or R$_2$—P(O)-L-P(O)—R$_2$, wherein each R is independently hydrogen, alkyl, cycloalkyl, alkenyl, aryl, aralkyl, or heteroaryl, and wherein L is a divalent group including alkanediyl, cycloalkanediyl, alkenediyl, arenediyl, aralkanediyl, or heteroarenediyl. The term "phosphine oxide" also includes oxides of the phosphines described in U.S. Pat. App. Pub. No. 2006/0173212. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. The term "about" when used in the context of epoxidation process conditions is used to imply the natural variation of conditions and represent a variation of plus or minus 5% of the measurement. In some embodiments, the variation is plus or minus 1% of the measurement.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

An "isomer" of a first compound is a separate compound in which each molecule contains the same constituent atoms as the first compound, but where the configuration of those atoms in three-dimensional space differs.

A "method" is series of one or more steps undertaken for producing to a final product, result or outcome. As used herein, the word "method" is used interchangeably with the word "process."

The above definitions supersede any conflicting definition(s) in any reference that is incorporated by reference herein. The fact that certain terms are defined, however, should not be considered as indicative that any term that is undefined or indefinite. Rather, all terms used are believed to describe the technology in terms such that one of ordinary skill can appreciate the scope and practice the present technology.

EXAMPLES

The following examples are included to demonstrate embodiments of the present technology. It should be appreciated by those of skill in the art that the techniques disclosed in the examples which follow represent techniques discovered by the inventors to function well in the practice of the technology. However, those of skill in the art should, in light of the present disclosure, appreciate that many changes can be made in the specific embodiments which are disclosed and still obtain a like or similar result without departing from the spirit and scope of the technology.

Example 1

Carbonylation of Methyl Acetate

The experiments described below were carried out in batch mode using a 300 mL autoclave constructed of Hastalloy C-276. The reactor head was equipped with attachments for cooling coils, thermocouples and dip tubes for sample exit and return. Loss of vapor to the vapor stack was minimized by two in-series condensers. The reaction components minus the catalyst were charged to the reactor. After leak testing with nitrogen and purging with $CO-N_2$ 50%-50%, the reactor and its contents were heated to the desired temperature at a $CO-N_2$ pressure of 100-200 psig (689-1,379 kPa) with agitation.

The reaction was then started by injecting rhodium-containing catalyst into the reactor and then raising the pressure of the reactor to 400 psig (2,758 kPa). The reaction was allowed to proceed at constant pressure, which was maintained by feeding 50%-50% $CO-N_2$ from a high pressure reservoir via regulator. The extent of the carbonylation reaction was measured by the pressure drop in the reservoir. The pressure drop was converted to moles of CO reacted using the known reservoir volume. At run termination, when no further CO uptake was observed, the batch reactor was cooled and a sample removed for gas chromatographic analysis.

The data associated with Runs #1-4 as contained in Table 1 were obtained in which all of the following components, unless otherwise specified, were added to the reactor:
3 M $H_2O$
0.5 M HI
0.7 M methyl acetate
4.4 mM Rh
22 mM Ru
0.5 M TPPO The following conditions were common to all runs: 175° C. and 400 psig (2,758 kPa) ($CO-N_2$, 50%-50%). Rhodium was added to the reaction as rhodium acetate. When ruthenium was added to the reaction, the metal was added as ruthenium acetate.

In Table 1, the column labelled "STY" refers to space-time-yield which has units of moles·$L^{-1}$·$hr^{-1}$. This rate measurement is associated with the initial period of the reaction during which component concentrations have not changed substantially from their starting concentrations and in which CO uptake varies linearly with time elapsed. The column labelled "% HOAc Yield" refers to the total amount of acetic formed over the course of the run, as measured by CO consumption, as a percentage of the theoretical maximum acetic that could form based on starting methyl acetate concentration.

As can be seen by comparing Runs #1 and #2 of Table 1, the addition of ruthenium to the reaction where no phosphine oxide is present leads to a slight increase in yield and space-time yield but also a 1.6 fold increase in by-product propionic acid formation. In contrast, when comparative runs are carried out with phosphine oxide present as shown in Runs #3 and #4, the slight increase in yield and space-time yield with addition of ruthenium is again observed but is now accompanied by a 2.5 fold decrease in propionic acid formation.

TABLE 1

Results of Carbonylation of Methyl Acetate Using Ruthenium and Phosphine Oxide Additives

| Run # | Phosphine Oxide (M) | Ru, mM | STY | % HOAc Yield | Propionic Acid, ppm |
|---|---|---|---|---|---|
| 1 | 0 | 0 | 1.48 | 37 | 180 |
| 2 | 0 | 22 | 1.81 | 42 | 280 |
| 3 | 0.5 | 0 | 1.49 | 34 | 100 |
| 4 | 0.5 | 22 | 1.64 | 41 | 40 |

All of the compounds, complexes, and methods disclosed and claimed herein can be made and executed without undue experimentation in light of the present disclosure. It will be apparent to those of skill in the art that variations may be applied to the compounds, complexes, and methods describe herein, as well as in the steps or in the sequence of steps of the method described herein without departing from the concept, spirit, and scope of the technology. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the technology as defined by the appended claims.

REFERENCES

The following references to the extent that they provide exemplary procedural or other details supplementary to those set forth herein, are specifically incorporated herein by reference.
U.S. Pat. No. 5,817,869
U.S. Pat. No. 6,031,129
U.S. Pat. No. 6,573,403
U.S. Pat. No. 7,053,241
US Pat. App. Pub. No. 2006/0173212
Anderson, N. G., *Practical Process Research & Development—A Guide for Organic Chemists*, $2^{nd}$ ed., Academic Press, New York, 2012.

What is claimed is:

1. A method for producing acetic acid comprising reacting:
   (A) a starting material selected from the group consisting of methanol, dimethyl ether and methyl acetate;
   (B) carbon monoxide; and
   (C) a rhodium compound;
   in a reaction mixture in the presence of a ruthenium compound at a rhodium to ruthenium ratio of about 0.1:1 to about 20:1, a first iodide source, and a phosphine oxide, where C≤24, under conditions sufficient to cause carbonylation to produce acetic acid, and comprising maintaining 10-114 equivalents of the phosphine oxide, where C≤24, relative to the rhodium complex in the reaction mixture.

2. The method of claim 1, wherein the rhodium compound is rhodium(II) acetate, rhodium(III) acetate, $Rh_2(CO)_4I_2$, $Rh_2(CO)_4Br_2$, $Rh_2(CO)_4Cl_2$, or $[H][Rh(CO)_2I_2]$.

3. The method of claim 1, wherein the ruthenium compound is ruthenium acetate or ruthenium iodide.

4. The method of claim 1, wherein the phosphine oxide, where C≤24, is triphenylphosphine oxide.

5. The method of claim 1, comprising maintaining greater than 50 equivalents of the phosphine oxide, where C≤24, relative to the rhodium complex in the reaction mixture.

6. The method of claim 1, wherein the methyl acetate is maintained at a concentration from 0.1 M to 5 M.

7. The method of claim 1, wherein the first iodide source is hydroiodic acid.

8. The method of claim 1 comprising maintaining the first iodide source at a concentration from 0.05 M to 2.0 M.

9. The method of claim 1 further comprising adding a second iodide source.

10. The method of claim 9, wherein the second iodide source is methyl iodide.

11. The method of claim 9 comprising maintaining the second iodide source at a concentration from 0.05 M to 3 M.

12. The method of claim 1, wherein the method further comprises adding water to the reaction.

13. The method of claim 12, wherein the water is maintained at a concentration less than 7.5 M.

14. The method of claim 1, wherein the method comprises heating the reaction to a temperature from 50° C. to 300° C.

15. The method of claim 1, wherein the method comprises running the reaction at a pressure from 200 psig (1,378 kPa) to 600 psig (4,137 kPa).

16. The method of claim 1, further comprising adding hydrogen gas to the reaction.

17. The method of claim 1, wherein the rhodium to ruthenium ratio is about 0.5:1 to about 10:1.

18. The method of claim 1, wherein the rhodium to ruthenium ratio is about 2:1 to about 10:1.

* * * * *

UNITED STATES PATENT AND TRADEMARK OFFICE
CERTIFICATE OF CORRECTION

Page 1 of 1

PATENT NO. : 9,822,054 B2
APPLICATION NO. : 14/997654
DATED : November 21, 2017
INVENTOR(S) : Noel C. Hallinan et al.

It is certified that error appears in the above-identified patent and that said Letters Patent is hereby corrected as shown below:

On the Title Page

Item (73) Line 1 Delete "Acetyis," and insert --Acetyls,--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*